US00PP29504P3

(12) United States Plant Patent
Ranney

(10) Patent No.: US PP29,504 P3
(45) Date of Patent: Jul. 17, 2018

(54) ***BERBERIS* PLANT NAMED 'NCBX1'**

(50) Latin Name: ***Berberis thunbergii* x *Berberis media***
Varietal Denomination: NCBX1

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 52 days.

(21) Appl. No.: 14/999,516

(22) Filed: May 18, 2016

(65) Prior Publication Data

US 2017/0339810 P1 Nov. 23, 2017

(51) Int. Cl.
*A01H 5/02* (2018.01)
*A01H 5/08* (2018.01)

(52) U.S. Cl.
USPC ..... Plt./241
CPC ..... *A01H 5/08* (2013.01)

(58) Field of Classification Search
USPC ..... Plt./241
See application file for complete search history.

*Primary Examiner* — Keith O Robinson
(74) *Attorney, Agent, or Firm* — Cassandra Bright

(57) ABSTRACT

A new and distinct *Berberis* cultivar named 'NCBX1' is disclosed, characterized by glossy purple foliage and a very compact plant habit. Plants have no observed female fertility. The new variety is a *Berberis*, normally produced as an outdoor garden plant.

2 Drawing Sheets

Figure 1:
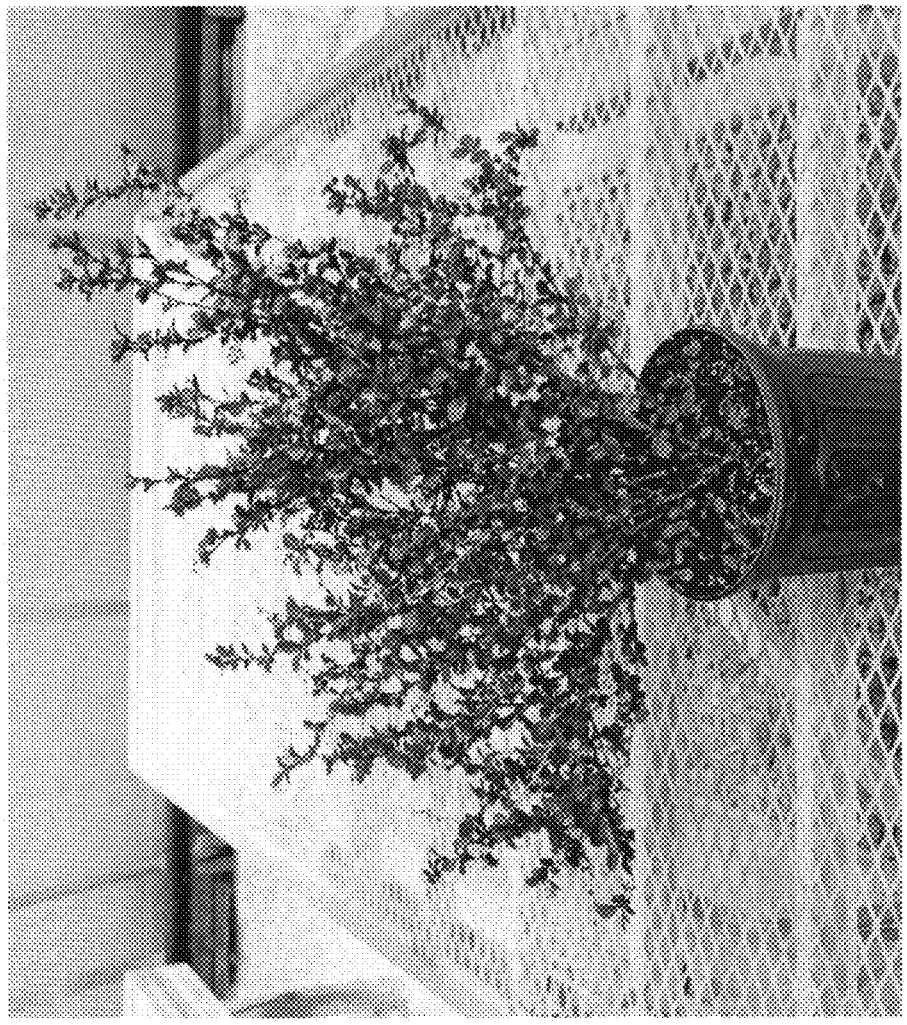

Latin name of the genus and species: *Berberis thunbergii* x *Berberis media.*

Variety denomination: 'NCBX1'.

BACKGROUND OF THE INVENTION

The new *Berberis* cultivar is a product of a planned breeding program conducted by the inventor, Thomas Ranney, in Mills River, N.C. The objective of the breeding program was to produce new *Berberis* varieties with purple foliage, compact plant forms and low fertility. The cross resulting in this new variety was made during Spring of 2004.

The seed parent is the unpatented, *Berberis* x *media* 'Red Jewel'. The pollen parent is the unpatented *Berberis thunbergii* 'Condorde'. The new variety was identified as a potentially interesting selection in Summer of 2005, at a research nursery in Mills River, N.C.

Asexual reproduction of the new cultivar 'NCBX1' by stem cuttings was first performed during the Summer of 2007, at a research nursery in Mills River, N.C. Subsequent propagation has shown that the unique features of this cultivar are stable and reproduced true to type in three successive generations.

SUMMARY OF THE INVENTION

The cultivar 'NCBX1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCBX1' These characteristics in combination distinguish 'NCBX1' as a new and distinct *Berberis* cultivar:

1. Glossy purple foliage.
2. Very compact habit.
3. No observed female fertility.

PARENT COMPARISON

Plants of the new cultivar 'NCBX1' are similar to plants of the seed parent in most horticultural characteristics, however, plants of the new cultivar 'NCBX1' differ in the following;

1. The new variety has not exhibited any female fertility, whereas the seed parent has a low female fertility rate.
2. While the seed parent has a compact plant form, plants of the new variety are even more compact.

Plants of the new cultivar 'NCBX1' are similar to plants of the pollen parent in most horticultural characteristics, however, plants of the new cultivar 'NCBX1' differ in the following;

1. The new variety has not exhibited any female fertility, whereas the pollen parent has a moderate female fertility rate.
2. The new variety has a more compact habit than the pollen parent.
3. The new variety has glossier foliage than the pollen parent.

COMMERCIAL COMPARISON

Plants of the new cultivar 'NCBX1' can be compared to the unpatented commercial variety *Berberis* 'Emerald Carousel'. These varieties are similar in most horticultural characteristics; however 'NCBX1' differs in the following:

1. Compact plant habit, whereas the comparator is a large plant with a spreading habit.
2. Burgundy/red leaf color, whereas the comparator has a green leaf color.

3. Very low female fertility, whereas the comparator is highly fruitful.
4. Foliage of the new variety is glossy, foliage of 'Emerald Carousel' is matte.

BRIEF DESCRIPTION OF THE PHOTOGRAPHS

The accompanying photograph in FIG. 1 illustrates in full color a typical plant of 'NCBX1' grown in a 1 gallon container.

Figure 2:
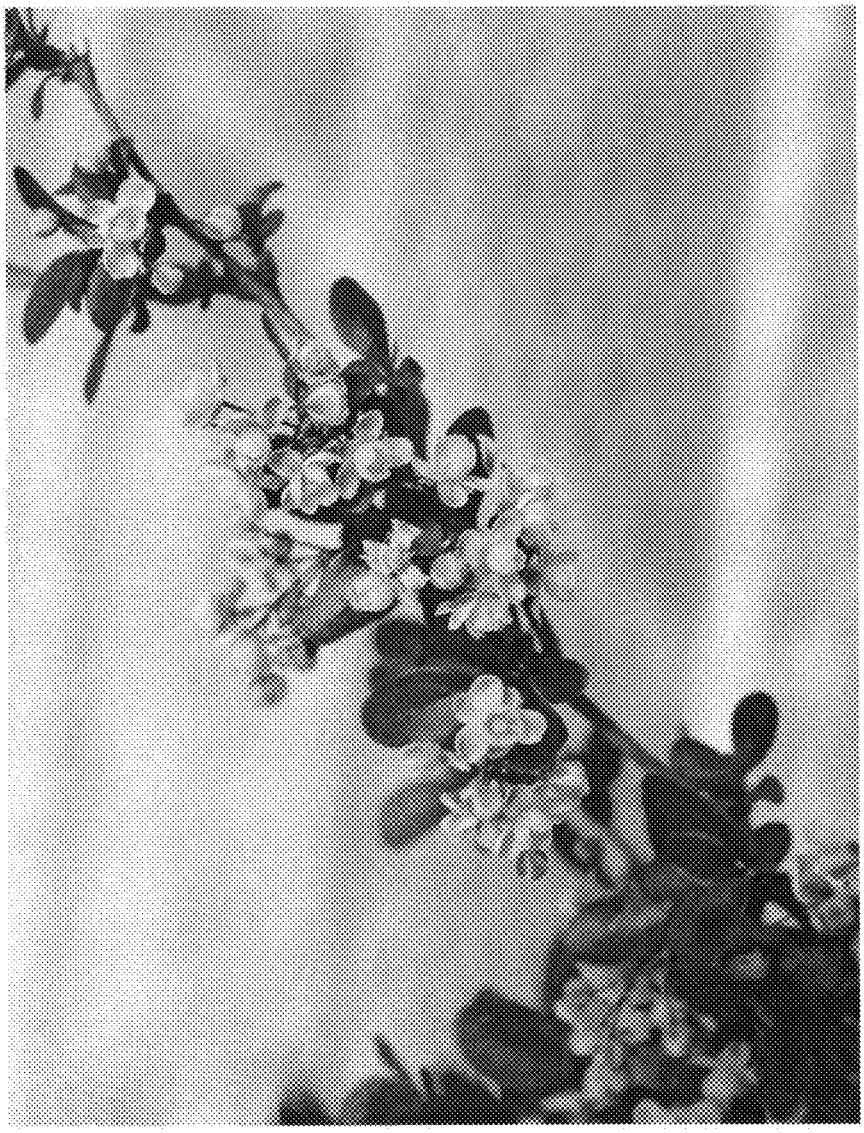

FIG. 2 illustrates a flowering branch of 'NCBX1' in a three gallon nursery container. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'NCBX1' plants grown outdoors in a research nursery in Mills River, N.C. Measurements were taken during the Spring and Summer of 2015. The plants were 2-3 years old, field grown. The growing temperature ranged from approximately −10° C. to 35° C. Measurements and numerical values represent averages of typical plant types.

Botanical classification: *Berberis thunbergii* x *Berberis media* 'NCBX1'.

PROPAGATION

Time to initiate roots: About 20 days at approximately 27° C.

Root description: Density is moderate to dense, fibrous, freely branching. Medium root thickness. White to brown in color, not effectively measured with a color chart.

Time to produce a rooted young plant: About 90 days at 27° C.

PLANT

Plant type: Perennial shrub. Semi-Evergreen.
Age of plant described: Approximately 2-3 years old.
Growth habit: Compact.
Pot size of plant described: Field grown plants.
Overall plant shape: Upright and rounded.
Height: 30 cm.
Plant spread: 30 cm.
Growth rate: Moderate.
Plant vigor: Good.
Branching characteristics: Alternate whorled.
Length of primary lateral branches: Average 14 cm, typical range 9 to 20 cm.
Diameter of lateral branches: 1 to 2 mm.
Quantity of lateral branches: Average 30.
Lateral branches:
- *Appearance*.—Matte.
- *Strength*.—Strong.
- *Color*.—Near RHS Greyed-Purple 187B.
- *Pubescence*.—None.

Internode length: Average 10 mm, typical range 8 to 12 mm.

FOLIAGE

Leaf:
- *Arrangement*.—Alternate whorled, single.
- *Leaf shape*.—Spatulate.
- *Average length*.—14 mm, typical range 8 to 19 mm.
- *Average width*.—8 mm, typical range 5 to 10 mm.
- *Apex*.—Mucronate.
- *Base*.—Attenuate.
- *Margin*.—Entire.
- *Texture of top surface*.—Smooth, glabrous.
- *Texture of bottom surface*.—Smooth, glabrous.
- *Appearance*.—Glossy upper surface. Lower surface mostly matte.
- *Color*.—Young foliage upper side: Near RHS Greyed-Purple 183A. Young foliage under side: Near RHS Greyed-Purple 183D. Mature foliage upper side: Near RHS Greyed-Purple 187A. Mature foliage under side: Near RHS Greyed-Purple N187B. Venation: Pattern: Pinnate, irregular. Color upper side: Near RHS Greyed-Purple 187A. Color under side: Near RHS Yellow-Green 144B.
- *Petiole*.—Average Length: 1 mm. Diameter: 1 mm. Petiole color upper side: Near RHS Greyed-Purple 187A. Petiole color lower side: Near RHS Greyed-Purple 187A. Petiole Texture upper side: Smooth. Petiole Texture lower side: Smooth.
- *Foliage durability*.—Foliage very durable to stress.
- *Spines*.—Simple. Form: Attached to plant nodes, occurring 1 to 3 per node. Size: Average 6 mm long, typical range 3 to 8 mm. Less than 1 mm wide. Color: Near RHS Yellow-Green 144B.

FLOWER

Natural flowering season: Spring.
Inflorescence type and habit: Umbellate fascicles. Axial, occurring on underside of branches.
Flower longevity on plant: 2 weeks.
Quantity of flowers per inflorescence: 3 to 8.
Quantity of flowers per plant: 500 to 1000.
Individual flowers:
- *Flower shape*.—Star shaped.
- *Flower aspect*.—Outwardly drooping.
- *Flowering arrangement*.—Terminal.
- *Size*.—Diameter: Approximately 5 mm. Depth: Approximately 9 mm.
- *Flower other characteristics*.—Persistence: Self cleaning. Fragrance: None.

Bud:
- *Shape*.—Rounded, globose.
- *Length*.—3 to 4 mm.
- *Diameter*.—3 to 4 mm.
- *Color*.—Near RHS Greyed-purple 187A.

Petal:
- *Petal arrangement*.—Whorl.
- *Number of petals per flower*.—5-6.
- *Petal shape*.—Elliptic.
- *Petal base*.—Obtuse.
- *Margin*.—Entire.
- *Tip shape*.—Obtuse.
- *Length*.—4 mm.

*Width.*—3 mm.
*Texture.*—Upper: Smooth. Lower: Smooth.

Petal color:
*When opening.*—Upper surface: Near RHS Yellow 12C flushed Red 46A. Lower surface: Near RHS Yellow 12C.
*Fully opened.*—Upper surface: Near RHS Yellow 12A. Lower surface: Near RHS Yellow 12C.

Sepal:
*Arrangement.*—Whorl.
*Appearance.*—Smooth.
*Number.*—6.
*Shape.*—Roughly orbicular.
*Tip.*—Acute to obtuse.
*Base.*—Acute to obtuse.
*Margin.*—Entire.
*Length.*—4 mm.
*Width.*—3 mm.
*Texture, upper.*—Smooth.
*Texture, lower.*—Smooth.
*Color.*—Upper surface at maturity: Near RHS Yellow-green 145B. Under surface at maturity: Near RHS Yellow-green 145B.

Peduncle:
*Length.*—6 mm.
*Diameter.*—Less than 1 mm.
*Color.*—Near RHS Yellow-Green 146B.
*Orientation.*—Upright/outward.
*Strength.*—Good.
*Texture.*—Smooth/glabrous.

REPRODUCTIVE ORGANS

Stamens:
*Number.*—6.
*Filament length.*—About 1 mm.
*Filament color.*—Near RHS green 137B.

Anthers:
*Shape.*—Globular.
*Length.*—About 1 mm.
*Color.*—Near RHS Yellow 12A.
*Pollen color.*—Near RHS Yellow 12A.
*Pollen amount.*—Moderate.

Pistil:
*Number.*—1 per flower.
*Length.*—About 3 mm.
*Style.*—Length: About 3 mm. Color: Near RHS Red 46A.
*Stigma.*—Color: Near RHS Yellow 2A.

OTHER CHARACTERISTICS

Seeds and fruits: Not observed to produce seed.
Disease/pest resistance: Neither resistance nor susceptibility to normal diseases and pests of *Berberis* have been observed.
Temperature tolerance: The new variety tolerates temperatures between −31° C. to 38° C.
Environmental stressors: Good resistance to wind and rain.

What is claimed is:

1. A new and distinct cultivar of *Berberis* plant named 'NCBX1' as herein illustrated and described.

* * * * *